(12) United States Patent
Tisserat

(10) Patent No.: US 7,160,706 B2
(45) Date of Patent: Jan. 9, 2007

(54) TISSUE CULTURE OF PLANT MATERIAL ENRICHED IN SECONDARY METABOLITES

(75) Inventor: Brent H. Tisserat, Metamora, IL (US)

(73) Assignees: The United States of America as represented by the Secretary of Agriculture, Washington, DC (US); The Biotechnology Research & Development Corp., Peoria, IL (US)

( * ) Notice: Subject to any disclaimer, the term of this patent is extended or adjusted under 35 U.S.C. 154(b) by 232 days.

(21) Appl. No.: 10/430,591

(22) Filed: May 6, 2003

(65) Prior Publication Data

US 2004/0221506 A1 Nov. 11, 2004

(51) Int. Cl.
*C12P 17/16* (2006.01)

(52) U.S. Cl. .................................................. 435/118
(58) Field of Classification Search .................. 435/118
See application file for complete search history.

(56) References Cited

U.S. PATENT DOCUMENTS 6,060,314 A    5/2000   Tisserat et al.

OTHER PUBLICATIONS

Ilahi, I et al., Regenerating in cultures of *Papaver bracteatum* as influenced by growth hormones and temperature, 1994, Plan Cell, Tissue and Organ Culture (38) p. 81–83.*
Tisserat, B et al., "Influence of Ultra–high Levels of Carbon Dioxide on Secondary Metabolite Production in Vitro," Jun. 1999, HortScience, vol. 34(3), #563, p. 543.*
Hirata, K. et al., "Production of Indole Alkaloids in Multiple Shoot Culture of *Catharanthus roseus* (L). G. Don." Agric. Biol. Chem., 1987, 51 (5), p. 1311–1317.*
Margaret F. Roberts, Isoquinolines (*Papaver* Alkaloids), Cell Culture and somatic Cell Genetics of Plants, Academic Press, Inc., vol. 5, pp. 315–334 (1998).
T. Lorenz et al., Production of Morphine Alkaloids: (S)–nor-laudanosoline, a Key Intermediate, Enzyme Microb. Technol., vol. 10, pp. 219–226 (1988).
Kathryn K. Kamo et al., Morphinane Alkaloids in Cultured Tissues and Redifferentiated Organs of *Papaver Somniferum*, Phytochemistry, vol. 21, No. 1, pp. 219–222 (1982).
R. Schuchmann et al., Somatic Embryogenesis of Tissue Cultures of *Papaver somniferum* and *Papaver orientale* and It's Relationship to Alkaloid and Lipid Metabolism, Plant Cell Reports, 2:88–91 (1983).
T.M. Kutchan et al., Cytodifferentiation and Alkaloid Accumulation in Cultured Cells of *Papaver bracteatum*, Plant Cell Reports 2:281–284 (1983).
T. Yoshikawa et al., Regeneration and in Vitro Flowering of Plants Derived from Callus Cultures of Opium Poppy (*Papaver somniferum*), Experientia, 39:1031–1033 (1983).
Abdelmajid Kassem et al., Somatic Embryogenesis, Rhizogenesis, and Morphinan Alkaloids Production in Two Species of Opium Poppy, J. Biomedicine and Biotechnology, 1:2, pp. 70–78 (2001).
K.B. Day et al., Plant Regeneration and thebaine Content of Plants Derived from Callus Culture of *Papaver bracteatum*, Plant Cell Reports, 5:471–474 (1986).
E.G. Alkhimova et al., Production of medicinal Alkaloids by *Papaver Bracteatum Cultured Cells*, Acta Horticulturae 330, Medicinal and Aromatic Plants, pp. 287–288 (1993).
Brent Tisserat, Growth Responses and Construction Costs of Various Tissue Culture Systems, Technology & Product Reports, Hort Technology, pp. 62–68, Jan./Mar. 1996.
Samuel Galewsky, Synthesis of Morphinane Alkaloids During Opium Poppy Somatic Embryogenesis, Plant Science, 45:215–222 (1986).

* cited by examiner

*Primary Examiner*—Bruce R. Campell
*Assistant Examiner*—Susan B. McCormick-Ewoldt
(74) *Attorney, Agent, or Firm*—John D. Fado; Curtis P. Ribando; Randall E. Deck

(57) ABSTRACT

Plant material enriched in secondary metabolites is produced in tissue culture under conditions that organogenically produce a proliferation of shoots and leafy material, and harvesting the leafy material and shoots while in a green, actively-growing, non-senescent stage. Of particular interest is plant material that produces alkaloids, especially material from poppy (*Papaver* sp.) that will yield economically attractive levels of morphinane alkaloids, particularly thebaine.

17 Claims, No Drawings

TISSUE CULTURE OF PLANT MATERIAL ENRICHED IN SECONDARY METABOLITES

BACKGROUND OF THE INVENTION

1. Field of the Invention

This invention relates to a tissue culture method for abundant production of plant material rich in secondary metabolites, particularly alkaloids of principal interest is a method for culturing poppy plants useful for yielding high levels of morphinan alkaloids, especially thebaine.

2. Description of the Prior Art

The advantages of applying tissue culture to the production of plants rich in secondary metabolites having economic importance are multi-fold. In tissue culture, germination, growth and harvesting are not dependent on season, climate or other specific environmental growth conditions. Moreover, in tissue culture, plants are more readily protected from insects, disease, and adverse weather phenomena.

M. Roberts [*Cell Culture and Somatic Cell Genetics of Plants*, Vol. 5, (1988) in Academic Press Inc., pp. 315–334] reviews the role of tissue culture in the production of isoquinolines (*Papaver* alkaloids). This review notes that *Papaver* species produce a wide range of isoquinolines, and within the individual species there is considerable intraspecific variation in alkaloid content [Phillipson, J. D. (1983) *Planta Medica* 48:187–192]. Roberts points to *P. somniferum* L. and *P. bracteatum* Lindl as the major producers of morphinans (thebaine, codeine and morphine), the most important group of isoquinolines from a commercial and pharmaceutical standpoint. These opiates have been difficult to produce in plant cell cultures.

Lorenz, R. L. et al. [*Enzyme Microb. Technol.* (1988), 10:219–226] teach that, while the ratio of codeine to morphine can vary, the latex of most *P. somniferum* varieties will always contain both alkaloids. It is therefore not possible to produce codeine without creating a supply of morphine, most of which enters the illicit drug trade as heroin. Lorenz et al. additionally notes that thebaine, an intermediate on the biosynthetic pathway to codeine and morphine, has become important because it is not addictive and can easily be converted to codeine.

Kamo, K. K. et al. [*Phytochemistry* 21:219–222 (1982)] explored the influence of the natural plant hormones indoleacetic acid (IAA), isopentenyl adenine (IPA) or the synthetic hormones kinetin (K) and naphthaleneacidic acid (NAA) on the capacity of *P. somniferum* callus tissues, meristemoids, and redifferentiated roots and shoots to synthesize morphinane alkaloids on artificial media. Kamo et al. found that alkaloid synthesis in tissues appeared to be related to the growth rate of tissues. Fast-growing tissues, such as those grown on IPA or K, had relatively low alkaloid concentrations compared to slow-growing tissues cultured on combinations of K and NAA, or IPA and IAA. Also, shoot organs redifferentiated on callus produced greater quantities of morphinane alkaloids than the callus, itself, though the level of production was less than for shoots of intact seedlings.

Schuchmann, R. et al. [*Plant Cell Reports* (1983) 2:88–91] reports that the alkaloid patterns of in vitro regenerated plantlets were at least qualitatively similar to those of normally grown seedlings. Thebaine accumulated up to 0.2% by weight of dry matter. In normally-grown seedlings of the same size, thebaine levels were 0.03% (7-day) and 0.01% (26-day).

Kutchan, T. M. et al. [*Plant Cell Reports* (1983) 2:281–284] extracted thebaine from *P. bracteatum* green shoots and meristemoids in static culture at levels that were comparable to some of the highest levels previously reported. These results were obtained by initially growing the tissues in the presence of 5 ppm 6-benzylaminopurine (BA) or 2 ppm indolebutyric acid (IBA) and then transferring them to media without 2,4-dichlorophenoxyacetic acid (2,4-D), BA or IBA. The levels of thebaine were still generally three orders of magnitude lower than amounts in latex-containing mature flower stems.

In a study focused on the effects of photoperiod and temperature on in vitro regeneration of plantlets from callus cultures of *P. somniferum*, Yoshikawa, T. et al. [*Experientia* (1983) 39:1031–1033] observed that callus was actively promoted at 16–18° C., but inhibited at >25° C. Shoots grown at 16–18° C. grew to 10–15 cm and leaves appeared normal.

Day, K. B. et al. [*Plant Cell Reports* (1986) 5:471–474] observed that plants regenerated from embryogenic callus cultures of two varieties of *P. bracteatum* and transplanted to soil yielded thebaine concentrations comparable to those in seed-grown plants. Green shoots up to 8 mm long were produced from some of the white meristemoid regions within 3–4 weeks of transfer to solidified Murahige and Skoog (MS) medium. Thebaine levels of plantlets cultivated on MS medium remained modest, but increased significantly when the plantlets were transferred to soil and grown in the greenhouse. The leaves of one particular plant produced 517 µg thebaine/g fresh weight after 5 months on MS plus 5 months in the greenhouse.

Kaseem, M. A. et al. [*J. Biomedicine and Biotechnology* 1:2 (2001) 70–78] observed that stems and leaves or explants from seed-grown *P. somniferum* album contained morphine (0.023%), codeine (0.013%) and thebaine (0.017%). Similar results were obtained with *P. somniferum*.

SUMMARY OF THE INVENTION

We have now invented a method for producing plant material enriched in a secondary metabolite comprising the steps:

a. providing shoot material of the plant;
b. culturing the shoot material in tissue culture under conditions that organogenically produce a proliferation of shoots and leafy material; and
c. harvesting the shoots and leafy material while the leafy material is in a green, actively-growing, non-senescent stage and when the shoots and leafy material are enriched in the secondary metabolite.

In accordance with this invention, it is an object to provide a tissue culture method for consistently producing ample quantities of secondary plant metabolites.

It is a further object of this invention to provide a method for economical production of alkaloids in tissue culture.

It is also an object of the invention to cultivate species of *Papaver* under conditions that will yield economically attractive levels of morphinane alkaloids.

Another object of the invention is to provide an alternative to field-grown poppies as a source of morphinane alkaloids.

Yet another object of the invention is to provide a safe and plentiful supply of thebaine.

Other objects and advantages of this invention will become readily apparent from the ensuing description.

DETAILED DESCRIPTION

The method of this invention is deemed to be applicable to virtually any plant that naturally produces, or can be stimulated to produce, at least one secondary metabolite. Of particular interest are plants that produce isoquinolines, and especially alkaloids. Of greatest interest are plants that naturally produce, or can be stimulated to produce morphinan alkaloids or their precursors. Without limitation thereto, examples of nonmorphinan alkaloids as reported by Roberts, supra, include stylopine, orientalidine, sanguinarine, oxysanguinarine, dihydrosanguinarine, norsanguinarine, chelerubine, protopine, cryptopine, noscapine, isothebaine and magnoflorine. Without limitation thereto, examples of morphinan alkaloids and their precursors include as reported by Roberts, supra, include dopamine, (S)-norlaudanasoline, (S)-reticuline, 1,2-dehydroreticuline, (R)-reticuline, salutaridine, salutaridinol, thebaine, codeinone, codeine and morphine. Of particular interest herein is thebaine.

Plants that produce isoquinoline compounds typically belong to the genus *Papaver*, especially *P. somniferum* L. and *P. bracteatum* Lindl. Roberts, supra, mentions other species of *Papaver* that have been reported to produce morphinan alkaloids in low yield, including *P. figax* L., *P. setogeri*, D. C., *P. orentale* L., and *P. rhoeas* L., as well as herbarium material of *P. acrochaetum* Borm, *P. caucasicum* Bieb., *P. cylindricum* Cullen, *P. gracile* Boiss., and *P. persicum* Lind.

The first step of the inventive method is to provide shoot material of the plant to be cultured. In the horticultural sense, a shoot is the first vertical photosynthetic growth of a seedling or plant, or more broadly, any young stem with leaves or lateral branch growth. The origin of the shoot may be parental shoot material, crown material, embryogenic callus, or the like. The "crown" of a plant refers to the terminal meristem part above the soil (or growth medium) level where roots and stem join and from where new shoots are produced; the "crown" is also the top of the rootstock. Thus, in the normal sense of the term, shoots are distinct from leaves and roots. The shoots may be initially provided from germinated seed, or thereafter by proliferation of parental shoot material as described below.

In the next step of the method, the shoot material is cultured under conditions that organogenically produce a proliferation of shoots and associated leafy material, with minimal production of roots. That is, culture conditions are provided such that the original shoot material will morphogenically yield other shoots as offshoots (i.e. lateral branches) of that material, and the shoots will produce leafy material. Collectively, the proliferation of shoots and leafy material constitute an increase in biomass, with minimal expenditure of energy directed into the production of root material. Typically, the proliferation of shoots and leafy material in a given chamber is asynchronous; that is, not all plants and shoots are at the same stage of development at a given time, nor do they grow at the same rate.

Morphogenic proliferation of shoots and leaves can be accomplished by means of any of a variety of growth conditions or combinations thereof. The medium used preferably includes nutrients that foster growth of an explanted plant tissue, such as, for example, the macro- and micronutrients set forth in Murashige & Skoog, Physiol. Plant., 15, 473–497 (1962), which are hereinafter referred to as "MS salts". "MS salts" used in the context of the present invention include suitable concentrations of ammonium nitrate, boric acid, calcium chloride, cobalt chloride, cupric sulfate, $Na_2$-EDTA, ferrous sulfate, magnesium sulfate, manganese sulfate, molybdic acid, potassium iodide, potassium nitrate, potassium phosphate monobasic, sodium nitrate, sodium phosphate monobasic and zinc sulfate. Minimal MS salts used in the context of the present invention preferably include the following as the recited concentration: $NH_4 NO_3$ (1650 mg/l); $KNO_3$ (1900 mg/l); $CaCl_2.2H_2O$ (440 mg/l); $MgSO_4.7H_2O$ (370 mg/l); $KH_2PO_4$ (170 mg/l); KI (0.83 mg/l); $H_3BO_3$ (6.3 mg/l); $MnSO_4.4H_2O$ (22.3 mg/l); $ZnSO_4.7H_2O$ (8.6 mg/l); $Na_2.MoO_4.2H_2O$ (0.25 mg/l) $CuSO_4.5H_2O$ (0.025 mg/l); $CoSO_4.6H_2O$ (0.025 mg/l); $Na_2$-EDTA (37.3 mg/l); $FeSO_4.7H_2O$ (27.8 mg/l). Table I compares 'MS with salts' (dry powder medium) with 'MS with salts and vitamins' (dry powder medium), both of which are contemplated for use herein. Additionally, other components for use in the growth medium include glycine, glutamine, myo-inositol, nicotinic acid, pyridoxine HCl, sucrose, and thiamine, for example. The medium can also include components to cause or foster differentiation or dedifferentiation of the explanted tissues being propagated in the chamber. Such components include, but are not limited to, auxins, cytokinins and abscisic acid. The medium also is adjusted to a suitable pH range that is preferably greater than about 4 and less than about 6. In a preferred embodiment, the nutrient medium includes suitable buffering agents for maintained the pH at the desired level. These agents will typically have a pKa between about 4.5 and about 5.5, and include, but are not limited to, citric acid, N-morpholino-ethansulfonic acid, potassium hydrogen phthalate, and benzoic acid. The medium may be supplemented with a carbon nutrient, such as a sugar. Exemplary sugars include sucrose, glucose and fructose. The medium may also be supplemented with plant hormones, feeder compounds (e.g. amino acids) or other growth regulators, including, without limitation thereto, indoleacetic acid (IAA), isopentenyl adenine (IPA), kinetin (K) and naphthaleneacidic acid (NAA), 6-benzylaminopurine (BA) or 2 ppm indolebutyric acid (IBA), and 2,4-dichlorophenoxyacetic acid (2,4-D). Levels of growth regulators from about 0.01–1 mg/L are typical, with the level of NAA normally being about 0.01 mg/L and the levels of the other regulators normally being about 0.1 mg/L.

It is important for germination and also for the rapid proliferation of the shoot and leafy material of *Papaver* species for the temperature of the culture to be maintained at or below about 20° C., usually within the range of about 12–20° C., and preferably within the range of about 15–19° C. For most growth responses, 18.5° C. has been found to be optimal; though 15° C. may be more optimal for morphinan production. The tissue must also be exposed to sufficient light to promote greening of the leafy material. The level of light exposure would typically be within the range of about 25–250 PPFD (photosynthetic photon flux density; 1 PPFD=1 μmol $m^{-2}s^{-1}$), and preferably in the range of 100–200 PPFD.

In one embodiment of the invention, the desired growth response of the plant material is enhanced in an atmosphere of elevated carbon dioxide levels. This is especially true for *P. somniferum* cultures. For example, it is recommended that the $CO_2$ concentration exceeds 1000 μl/L, more preferably is from about 3000 μl/L to about 20,000 μl/L, yet more preferably is from about 7000 μl/L to about 12,000 μl/L. We have found that levels of $CO_2$ on the order of 10,000 μl/L resulted in growth of *P. bracteatum* shoots and seedlings at a level of 3.5-fold as compared to the growth at ambient air levels of $CO_2$. A suitable system for providing elevated levels of carbon dioxide to explants in tissue culture is described by Tisserat et al. in U.S. Pat. No. 6,060,314, herein incorporated by reference in its entirety.

In another embodiment of the invention, the explant material is grown in an automated plant culture system (APCS), or bioreactor, as described in detail by Tisserat [*HortTechnology* (1996) 6:62–68, herein incorporated by reference]. In the APSC, a plant culture is established and maintained in a chamber on an inert substrate. Medium containing nutrients sufficient for growth of the plant material is presented to the plant material by periodically immersing the inert substrate in the medium for a defined residence time as discussed below, thereby placing the plant material in contact with the medium, followed by the substantial removal of the medium from the inert substrate; the remainder of the time, i.e., between the residence times of immersion of the inert substrate in the nutrient medium, the plant material is in contact with the inert substrate and medium that is adhered by surface tension on the inert substrate. The inert substrate can be any suitable absorbent or non-absorbent material, and is preferably a non-absorbent material such as, but not limited to, glass, ceramic, stone, plastic; and the substrate can be any suitable shape or size, including spheres, cubes, or random shapes, each having an approximate longest dimension of length or diameter of, for example, from about 1 mm to about 5 mm. We have found that the poppy cultures grown in 1.8-L chambers exhibit larger leaves and greater proliferation of shoots than cultures grown in smaller chambers (365 ml) or in culture tubes (55 ml).

Airflow into the chamber is preferably controlled such that undesired microorganisms are not introduced and the carbon dioxide concentration is held at a desired level. Accordingly, the airflow into or out of the chamber is screened preferably by a filter having a pore size (0.2–0.45 μm) that precludes or substantially precludes passage of microbes. Similarly, the growth medium is preferably sterilized prior to initially entering the chamber, upon recovery from the chamber, and again prior to being recycled back into the chamber. Such sterilization of the medium can be effected by any suitable method, such as, but not limited to filtering, exposure to ozone or ultraviolet light, or heating, such as in an autoclave. It is contemplated, however, that the chamber and medium cooperate to sufficiently retard the growth of undesirable microbes and that, in one embodiment, no sterilization between periods of introducing the nutrient medium into the bioreactor is required.

The morphogenic shooting response for a given set of conditions varies among different *Papaver* cultivars. Table II shows the percent shooting responses of 24-week old *P. bracteatum* and *P. somniferum* L. shoot cultures maintained on MS medium with 0.1 mg/L BA and 0.01 mg/L NAA at 20° C. and ambient (350 μl/L) $CO_2$. These cultures were grown in 165 cc Magenta containers.

In the final step of the process, the leafy material and shoots are harvested while the leafy material is in a green, actively-growing, non-senescent stage. It is at this stage that the vegetative tissues and organs have high contents of secondary metabolites, such as isoquinolines, especially the aforementioned alkaloids, and are said to be enriched in these products. The levels of these compounds may equal or exceed levels found in tissues of soil-grown plants. The leaves of 8-week old soil grown plants will typically have alkaloids within the range of about 0.25–18 mg/g dry weight. For example, levels of thebaine exceeding 8 mg/g of harvested tissue have been obtained from 16-week old *P. somniferum* L. shoot material grown on MS salts and vitamins medium supplemented with 0.1 mg/L BA and 0.01 mg/L NAA. In general, it is expected that shoot and leafy material grown in tissue culture in accordance with the invention will have thebaine levels at the time of harvest greater than about 3 mg/g of harvested tissue, and preferably greater than about 5 mg/g. Though inflorescences occur in culture, they are not necessary for pharmaceutical production. Accordingly, harvest of the leaf and shoot material may take place prior to flowering, thereby reducing the complexity of the tissue culture procedures required to produce high amounts of pharmaceutical-yielding biomass.

The following examples are intended to further illustrate the invention, without any intent for the invention to be limited to the specific embodiments described therein. All references disclosed herein or relied upon in whole or in part in the description of the invention are incorporated by reference in their entirety.

EXAMPLE 1

Effects of Temperature and $CO_2$ Levels on Fresh Weight and Shoot Length

Culture tubes (25×150 mm) cooled by a rapid-cool refrigerated circulating bath set at 15° C., 18.5° C., 20° C. or 25° C. were charged with MS with salts and vitamins, and seeds of one of three different poppy cultivars were sprinkled on top of the media. Either ambient levels (350 μL/L) or elevated levels (10,000 μL/L) of $CO_2$ were passed through the chambers. After 8 weeks, the culture weight and average shoot length in each chamber were measured. The results are reported in Table III, below. Note that cultures maintained at 25° C. died before the 8-week incubation period was completed.

EXAMPLE 2

Effects of $CO_2$ Levels on Morphinan Alkaloid Production

Culture tubes (25×150 mm) subjected to temperature control as described in Example 1 were set up for either seedling or established shoot cultures on MS salts and vitamins. The seedling cultures were established from seed of *P. somniferum* L. "Persion White F2" and maintained at 20° C. for 8 weeks without the use of growth regulators. Shoot cultures of various cultivars of *P. somniferum* L. and *P. bracteatum* were established from cuttings of existing shoots and were grown on MS salts and vitamins without hormones at 20° C. with ambient air levels of $CO_2$ (350 μL/L) or elevated levels (10,000 μL/L) of $CO_2$. Liquid chromatography-Mass Spectrophotometry (LC-MS) system was employed to detect narcotic pharmaceutical compounds (morphinans). The results are shown in Table IV, below. In every case, thebaine levels produced at 10,000 μL/L of $CO_2$ were higher than those produced at 350 μL/L.

EXAMPLE 3

Morphinan Levels in Various *P. somniferum* L. Plant Tissue Culture Organs and as a Function of Various Culture Conditions All cultures in this Example were generated from *P. somniferum* L. and were maintained at 20° C. and ambient $CO_2$ levels (350 μL/L) Except as indicated, all cultures were conducted in 25×150 mm culture tubes containing 25 ml of MS with salts medium and were examined at 8 weeks. For the callus culture, the medium was supplemented with 0.1 mg/L 2,4-D and 0.1 mg/L BA. For the shoots grown in the dark, the medium was supplemented with 0.1 mg/L BA and 0.01 mg/L NAA. The two studies with 16 week-old shoots were carried out in 365-ml polycarbonate boxes, one study using the APCS described above, and the other one not using it (static culture chamber). For the 16-week old studies, the MS medium with salts was supplemented with 0.01 mg/L NAA. The results are reported in Table V, below.

TABLE I

Murashige and Skoog Media

| Component | Murashige and Skoog Salt Base (dry powder medium) | Murashige and Skoog Salt Basal Medium (dry powder medium) |
|---|---|---|
| INORGANIC SALTS | | |
| Calcium chloride anhydrous | 332.20 | 332.200 |
| Magnesium sulfate anhydrous | 180.70 | 180.700 |
| Potassium phosphate monobasic | 170.00 | 170.000 |
| Potassium iodide | 0.83 | 0.830 |
| Potassium nitrate | 1900.00 | 1900.000 |
| Ammonium nitrate | 1650.00 | 1650.000 |
| EDTA ferric sodium salt | 36.70 | 36.700 |
| Cobalt chloride hexahydrate | 0.03 | 0.025 |
| Cupric sulfate pentahydrate | 0.03 | |
| Manganous sulfate monohydrate | 16.90 | 16.898 |
| Sodium molybdate dihydrate | 0.03 | 0.025 |
| Zinc sulfate heptahydrate | 8.60 | 8.600 |
| VITAMINS | | |
| i-inositol | — | 100.000 |
| Niacin | — | 0.500 |
| Pyridoxine HCl | — | 0.500 |
| Thiamine HCl | — | 0.100 |
| AMINO ACIDS | | |
| Glycine | — | 2.000 |
| OTHER | | |
| Boric acid | 6.20 | 6.200 |
| Grams of powder per liter | 4.30 | 4.302 |

TABLE II

Percent Shooting Responses of 24-week Old *P. Bracteatum* and *P. Somniferum* L. Shoot Cultures

| Cultivar | % Dead | % Single | % Multiple | % 1 | % 2 | % 3 | % 4 | % 5 | % 6 | % 7 | % 8 | % 9 | % 10 | % <10 |
|---|---|---|---|---|---|---|---|---|---|---|---|---|---|---|
| P. bract. Cv. '374708' | 7.3 | 38.2 | 54.5 | 38 | 4 | 13 | 11 | 5 | 2 | 4 | 4 | 0 | 0 | 13 |
| P. bract. Cv. '374709' | 22.5 | 37.5 | 40.0 | 38 | 0 | 10 | 3 | 8 | 5 | 3 | 0 | 3 | 0 | 10 |
| P. bract. Cv. '374838' | 9.1 | 0.0 | 90.9 | 0 | 0 | 9 | 9 | 9 | 0 | 0 | 0 | 0 | 0 | 64 |
| P. bract. Cv. '381597' | 17.6 | 17.6 | 64.7 | 18 | 0 | 12 | 12 | 24 | 0 | 0 | 6 | 0 | 0 | 12 |
| P. bract. Cv. '414783' | 5.6 | 5.6 | 88.9 | 6 | 11 | 6 | 0 | 17 | 0 | 11 | 0 | 11 | 0 | 33 |
| P. som Cv. 'Hungarian Queen' | 34.6 | 34.6 | 30.8 | 35 | 8 | 0 | 4 | 0 | 4 | 0 | 4 | 4 | 4 | 4 |
| P. som. Cv. 'Persian White' | 0.0 | 50.0 | 50.0 | 50 | 13 | 0 | 13 | 13 | 0 | 0 | 0 | 0 | 0 | 25 |
| P. som. Cv. 'Spice Rack' | 10.5 | 5.3 | 84.2 | 5 | 0 | 5 | 5 | 11 | 0 | 0 | 5 | 5 | 0 | 5 |

TABLE III

Effects of Temperature and CO₂ Levels on Fresh Weight and Shoot Length

| Temperature (° C.) | CO₂ levels (μL/L) | Culture Wt. (g)[1] | Shoot length (mm)[1] |
|---|---|---|---|
| *P. somniferum* cv. Persian Princess | | | |
| 15 | 10,000 | 0.74 +/− 0.22 a | 75.6 +/− 1.03 a |
| 18.5 | 10,000 | 0.24 +/− 0.09 b | 62.1 +/− 0.73 a |
| 20 | 10,000 | 0.13 +/− 0.1 c | 43.75 +/− 1.18 b |
| 25 | 10,000 | — +/− — | — +/− — |
| 20 | 350 | 0.07 +/− 0.03 d | 31 +/− 3 c |
| *P. somniferum* cv. Hungarian Queen | | | |
| 15 | 10,000 | 0.4 +/− 0.16 a | 88.9 +/− 0.68 a |
| 18.5 | 10,000 | 0.16 +/− 0.06 b | 65 +/− 0.52 b |
| 20 | 10,000 | 0.1 +/− 0.04 c | 47.6 +/− 0.53 c |
| 25 | 10,000 | — +/− — | — +/− — |
| 20 | 350 | 0.05 +/− 0.02 d | 32.2 +/− 0.34 d |
| *P. bracteatum* cv. 374717 | | | |
| 15 | 10,000 | 0.05 +/− 0.05 a | 14.4 +/− 0.72 a |
| 18.5 | 10,000 | 0.04 +/− 0.07 a | 20.3 +/− 0.44 b |
| 20 | 10,000 | 0.02 +/− 0.04 b | 17.4 +/− 0.64 b |
| 25 | 10,000 | — +/− — | — +/− — |
| 20 | 350 | 0.02 +/− 0.03 b | 11.7 +/− 0.39 c |

[1]Mean separation by Student-Newmann-Keuls Multiple Range Test ($P < 0.05$). Values in the same column with the letters are not significantly different.

TABLE IV

Effects of CO₂ Levels on Morphinan Alkaloid Production

| Treatment | Plant Name | Tissue Type | Morphine | Codeine | Thebaine |
|---|---|---|---|---|---|
| 350 μL $CO_2$ $L^{-1}$ | P. som. 'Persian White F2' | Seedlings | 0.431 | 0 | 0.423 |
| 10,000 μL $CO_2$ $L^{-1}$ | P. som. 'Persian White F2' | Seedlings | 0.363 | 0 | 0.617 |
| 350 μL $CO_2$ $L^{-1}$ | P. som. 'Persian Princess' | Seedlings | 0.461 | 0 | 0.637 |
| 10,000 μL $CO_2$ $L^{-1}$ | P. som. 'Persian Princess' | Seedlings | 0.427 | 0 | 0.921 |
| 350 μL $CO_2$ $L^{-1}$ | P. som. 'Persian White F2' | Shoots | 0.352 | 0 | 0.452 |
| 10,000 μL $CO_2$ $L^{-1}$ | P. som. 'Persian White F2' | Shoots | 0.366 | 0 | 0.682 |
| 350 μL $CO_2$ $L^{-1}$ | *P. bracteatum* '414784' | Shoots | 0.344 | 0 | 0.365 |
| 10,000 μL $CO_2$ $L^{-1}$ | *P. bracteatum* '414784' | Shoots | 0.395 | 0 | 0.804 |
| 350 μL $CO_2$ $L^{-1}$ | *P. bracteatum* '?' | Shoots | 0.319 | 0 | 0.594 |
| 10,000 μL $CO_2$ $L^{-1}$ | *P. bracteatum* '?' | Shoots | 1.337 | 0.918 | 0.803 |
| 350 μL $CO_2$ $L^{-1}$ | *P. bracteatum* '386097' | Shoots | 1.44 | 1.2 | 1.08 |
| 10,000 μL $CO_2$ $L^{-1}$ | *P. bracteatum* '386097' | Shoots | 1.14 | 0.71 | 1.18 |
| 350 μL $CO_2$ $L^{-1}$ | *P. bracteatum* '381602' | Shoots | 0.42 | 0 | 0.62 |
| 10,000 μL $CO_2$ $L^{-1}$ | *P. bracteatum* '381602' | Shoots | 1.61 | 0 | 0.96 |
| 350 μL $CO_2$ $L^{-1}$ | *P. bracteatum* '381591' | Shoots | 1.86 | 0.69 | 0.91 |
| 350 μL $CO_2$ $L^{-1}$ | *P. bracteatum* '381599' | Shoots | 1.89 | 0 | 1.07 |

TABLE V

Morphinan Levels in Various *P. somniferum* L. Plant Tissue Culture Organs and as a Function of Various Culture Conditions

| Tissue Type | Morphine (mg/g) | Codeine (mg/g) | Thebaine (mg/g) |
|---|---|---|---|
| Callus | 0 | 0 | 0 |
| Shoots grown in Dark | 0 | 0 | 0 |
| Roots | 0 | 0 | 0 |
| Multiple inflorescences | 0 | 0 | 0.25 |
| 8 wk old shoots on BM without growth regulators | 0 | 0.45 | 2.97 |
| 8 wk old dead shoots grown without growth regulators | 0 | 0 | 0 |
| 16 wk old shoots in APCS with 0.1 mg/L BA & 0.01 mg/L NAA | 0 | 0.27 | 4.7 |
| 16 wk old shoots on BM with 0.1 mg/L BA & 0.01 mg/L NAA | 0 | 0.12 | 8.17 |
| 16 wk old dead shoots (dead leaves) with 0.1 mg/L BA & 0.01 mg/L NAA | 0 | 0 | 0 |

What is claimed is:

1. A method for producing plant material of a *Papaver* species having a thebaine level greater than 3 mg/g comprising the steps:
    a. providing shoot material of said plant;
    b. culturing said shoot material in tissue culture under conditions that organogenically produce a proliferation of shoots and leafy material; and
    c. harvesting said shoots and/or leafy material while said leafy material is in a green, actively-growing, non-senescent stage and when said shoots and/or leafy material have said thebaine at a level greater than 3 mg/g of said shoots and/or leafy material.

2. The method of claim 1, wherein said plant material is a species of *Papaver* selected from the group consisting of *P. somniferum* and *P. bracteatum*.

3. The method of claim 1, wherein one of said conditions is an elevated source of carbon dioxide as compared to ambient air levels of carbon dioxide.

4. The method of claim 3, wherein said elevated level of carbon dioxide is a concentration of carbon dioxide in excess of 1000 μl/L.

5. The method of claim 3, wherein said elevated level of carbon dioxide is a concentration of carbon dioxide in the range of 3000 μl/L to 20,000 μl/L.

6. The method of claim 3, wherein said elevated level of carbon dioxide is a concentration of carbon dioxide in the range of 7000 μl/L to 12,000 μl/L.

7. The method of claim 3, wherein said elevated level of carbon dioxide is a concentration of carbon dioxide of approximately 10,000 µl/L.

8. The method of claim 1, wherein one of said conditions is a culture medium comprising sugar.

9. The method of claim 8, wherein said sugar is selected from the group consisting of sucrose, glucose and fructose.

10. The method of claim 1, wherein one of said conditions is a temperature below 25° C.

11. The method of claim 10, wherein said temperature is below 20° C.

12. The method of claim 10, wherein said temperature is in the range of 12–19° C.

13. The method of claim 1, wherein one of said conditions is an auxin source.

14. The method of claim 13, wherein said auxin is naphthaleneacetic acid.

15. The method of claim 1, wherein said shoot material provided in step (a) is grown from seed.

16. The method of claim 1, wherein said shoot material provided in step (a) is plant explant material.

17. The method of claim 1, wherein said proliferation of shoots and leafy material is asynchronous growth.

* * * * *